United States Patent
Baloa Welzien et al.

(10) Patent No.: US 9,399,109 B2
(45) Date of Patent: Jul. 26, 2016

(54) CONTINUOUS POSITIVE AIRWAY PRESSURE (CPAP) THERAPY USING MEASUREMENTS OF SPEED AND PRESSURE

(71) Applicant: Breathe Technologies, Inc., Irvine, CA (US)

(72) Inventors: Leonardo Alberto Baloa Welzien, Lake Forest, CA (US); Enrico Brambilla, Irvine, CA (US); Samir S. Ahmad, San Diego, CA (US)

(73) Assignee: Breathe Technologies, Inc., Irvine, CA (US)

( * ) Notice: Subject to any disclaimer, the term of this patent is extended or adjusted under 35 U.S.C. 154(b) by 6 days.

(21) Appl. No.: 13/657,439

(22) Filed: Oct. 22, 2012

(65) Prior Publication Data

US 2013/0228181 A1 Sep. 5, 2013

Related U.S. Application Data

(63) Continuation-in-part of application No. 13/411,257, filed on Mar. 2, 2012.

(51) Int. Cl.
*A61M 16/00* (2006.01)
*A61M 16/20* (2006.01)
(Continued)

(52) U.S. Cl.
CPC ......... *A61M 16/107* (2014.02); *A61M 16/0051* (2013.01); *A61M 16/0069* (2014.02);
(Continued)

(58) Field of Classification Search
CPC ............ A61M 16/00; A61M 16/0057; A61M 16/0066; A61M 2016/0021; A61M 2016/0036; A61M 2016/205; A61M 2016/0069; A61M 2016/0027; A61M 2205/15; A61M 2205/3331; A61M 2205/3365; A61M 2230/005
USPC ............. 128/204.18, 204.21, 204.23, 204.24, 128/204.26
See application file for complete search history.

(56) References Cited

U.S. PATENT DOCUMENTS 5,072,729 A 12/1991 DeVries
5,134,995 A 8/1992 Gruenke et al.
(Continued)

FOREIGN PATENT DOCUMENTS

EP 722747 A2 7/1996
WO 2005016217 2/2005
WO WO 2005016217 A2 * 2/2005

OTHER PUBLICATIONS

International Search Report and Written Opinion for PCT/US2013/028069. Issued May 3, 2013.
(Continued)

*Primary Examiner* — Valerie L Woodward
*Assistant Examiner* — Douglas Sul
(74) *Attorney, Agent, or Firm* — Stetina Brunda Garred & Brucker (57) ABSTRACT

A respiratory assistance device is disclosed. There is a variable speed blower with an output, and a patient ventilation interface configured for fitment on a patient respiratory passageway. A gas passage conduit couples the output of the blower to the patient ventilation interface. A pilot line from the gas passage conduit is coupled to a piloted exhalation valve of the patient ventilation interface. A pressure sensor measures a mask pressure in the patient ventilation interface, and a blower speed sensor measures a speed of the blower. A pressure controller in communication with the pressure sensor and the blower speed sensor detects a patient inspiratory phase and a patient expiratory phase from at least one of the measured speed of the blower and a set speed of the blower. The pressure controller adjusts an operating speed of the blower and actuates the piloted exhalation valve based upon the measured mask pressure.

24 Claims, 8 Drawing Sheets (51) Int. Cl.
 *A61M 16/10* (2006.01)
 *A61M 16/06* (2006.01)

(52) U.S. Cl.
 CPC ............. *A61M16/06* (2013.01); *A61M 16/201* (2014.02); *A61M 16/0066* (2013.01); *A61M 16/20* (2013.01); *A61M 2016/0021* (2013.01); *A61M 2016/0027* (2013.01); *A61M 2205/15* (2013.01); *A61M 2205/18* (2013.01); *A61M 2205/3331* (2013.01); *A61M 2205/3355* (2013.01); *A61M 2205/3365* (2013.01); *A61M 2205/3368* (2013.01); *A61M 2205/42* (2013.01); *A61M 2205/502* (2013.01); *A61M 2205/505* (2013.01); *A61M 2205/52* (2013.01); *A61M 2205/581* (2013.01); *A61M 2205/583* (2013.01); *A61M 2205/8206* (2013.01)

(56) References Cited

U.S. PATENT DOCUMENTS

| | | | |
|---|---|---|---|
| 5,245,995 A | 9/1993 | Sullivan et al. | |
| 5,303,699 A | 4/1994 | Bonassa et al. | |
| 5,353,788 A | 10/1994 | Miles et al. | |
| 5,492,113 A | 2/1996 | Estes et al. | |
| 5,503,146 A | 4/1996 | Froehlich et al. | |
| 5,551,419 A | 9/1996 | Froehlich et al. | |
| 5,598,838 A | 2/1997 | Servidio | |
| 5,632,269 A * | 5/1997 | Zdrojkowski | 128/204.23 |
| 5,694,923 A | 12/1997 | Hete et al. | |
| 5,735,267 A | 4/1998 | Tobia | |
| 5,813,399 A | 9/1998 | Isaza et al. | |
| 5,860,418 A | 1/1999 | Lundberg | |
| 6,305,372 B1 | 10/2001 | Servidio | |
| 6,332,463 B1 | 12/2001 | Farrugia et al. | |
| 6,367,474 B1 | 4/2002 | Berthon-Jones | |
| 6,425,395 B1 | 7/2002 | Brewer et al. | |
| 6,536,432 B2 | 3/2003 | Truschel | |
| 6,571,599 B1 * | 6/2003 | Surjadi | A61M 16/00 73/1.62 |
| 6,571,795 B2 * | 6/2003 | Bourdon | 128/204.23 |
| 6,629,531 B2 * | 10/2003 | Gleason | A62B 18/08 128/205.25 |
| 6,817,361 B2 | 11/2004 | Berthon-Jones | |
| 7,013,361 B2 | 3/2006 | Liron | |
| 7,044,129 B1 | 5/2006 | Truschel et al. | |
| 7,137,389 B2 | 11/2006 | Berthon-Jones | |
| 7,270,128 B2 | 9/2007 | Berthon-Jones | |
| 7,438,073 B2 | 10/2008 | Delache et al. | |
| 7,469,698 B1 | 12/2008 | Childers | |
| 7,487,774 B2 | 2/2009 | Acker | |
| 7,717,113 B2 | 5/2010 | Andrieux | |
| 7,770,579 B2 | 8/2010 | O'Connor et al. | |
| 7,987,847 B2 | 8/2011 | Wickham et al. | |
| 8,069,854 B2 | 12/2011 | Colla et al. | |
| 2006/0065270 A1 | 3/2006 | Li | |
| 2006/0196508 A1 * | 9/2006 | Chalvignac | 128/204.23 |
| 2007/0017518 A1 * | 1/2007 | Farrugia et al. | 128/204.23 |
| 2008/0196723 A1 | 8/2008 | Tilley | |
| 2009/0301488 A1 | 12/2009 | Sun | |
| 2010/0078024 A1 * | 4/2010 | Andrieux et al. | 128/204.21 |
| 2010/0170513 A1 | 7/2010 | Bowditch et al. | |
| 2010/0180895 A1 | 7/2010 | Kwok et al. | |
| 2010/0319697 A1 * | 12/2010 | Farrugia et al. | 128/204.18 |
| 2011/0126832 A1 * | 6/2011 | Winter et al. | 128/204.21 |
| 2011/0126834 A1 | 6/2011 | Winter et al. | |
| 2011/0126835 A1 | 6/2011 | Winter et al. | |

OTHER PUBLICATIONS

European Search Report for EP 13 75 4710 mailed Aug. 4, 2015.
Extended European Search Report for EP13755704.7, mailed on Dec. 3, 2015.

* cited by examiner

CONTINUOUS POSITIVE AIRWAY PRESSURE (CPAP) THERAPY USING MEASUREMENTS OF SPEED AND PRESSURE

CROSS-REFERENCE TO RELATED APPLICATIONS

The present application is a continuation-in-part application of U.S. patent application Ser. No. 13/411,257 entitled "DUAL PRESURE SENSOR CONTINUOUS POSITIVE AIRWAY PRESSURE (CPAP) THERAPY," the entirety of the disclosure of which is incorporated by reference herein.

STATEMENT RE: FEDERALLY SPONSORED RESEARCH/DEVELOPMENT

Not Applicable

BACKGROUND OF THE INVENTION

1. Field of the Invention

The present disclosure relates generally to the treatment of respiratory and cardiovascular conditions, and more particularly, to methods and systems for pressure sensing based continuous positive airway pressure (CPAP) therapy selectively providing therapeutic pressure of breathable gas to a patient utilizing a pressure sensor on a ventilation mask.

2. Description of the Related Art

Mechanical ventilators comprise medical devices that either perform or supplement breathing for patients. Early ventilators, such as the "iron lung," created negative pressure around the patient's chest to cause a flow of ambient air through the patient's nose and/or mouth into the lungs. However, the vast majority of contemporary ventilators instead use positive pressure to deliver gas to the patient's lungs via a patient circuit between the ventilator and the patient. The patient circuit typically consists of one or two large bore tubes (e.g., 22 mm inner diameter for adults; 15 mm inner diameter for pediatrics) that interface to the ventilator on one end and a patient mask on the other end.

Ventilators may support either a single limb or a dual limb patient circuit. Single limb patient circuits are typically utilized for less acute clinical requirements such as the treatment of obstructive sleep apnea or respiratory insufficiency. In further detail, the single limb patient circuit, as its nomenclature suggests, involves gas flow from the ventilator to the patient and patient mask over a single conduit. The patient inspires fresh gas from the patient circuit, and expires carbon dioxide-enriched gas that is purged from the system through vent holes in the mask.

One particular application of ventilator devices is in the treatment of obstructive sleep apnea (OSA) syndrome, where the patient's upper airway narrows or collapses during sleep. There are repetitive pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles. In order to retain the patient's airway and ensure normal, uninterrupted breathing during sleep, continuous positive airway pressure (CPAP) therapy may be prescribed.

Generally, CPAP involves the application of positive pressure to open the patient's airway to prevent its collapse, as would otherwise occur during apnea. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. However, supplying positive pressure flow into the patient during the expiratory phase generates resistance to the patient's breathing efforts, causing discomfort. Furthermore, toward the end of the patient's expiratory phase, flow and pressure in the airway is naturally minimal, such that positive pressure can cause additional discomfort. Notwithstanding the clinician's best efforts to prescribe a CPAP treatment flow rate that minimizes such extraneous pressure augmentation while ensuring the proper splinting of the airway during inspiration, the patient is still subject to higher pressures than needed throughout the breathing cycle.

Partially in response to this deficiency, CPAP systems that varied the pressure augmentation depending on the patient flow, i.e., inspiration or expiration, were developed. One such system is described in U.S. Pat. No. 6,932,084 to Estes, et al., which is understood to involve pressure augmentation during inspiration and pressure relief during exhalation based upon a patient flow estimator. The delivered pressure, which itself is measured and utilized by a pressure controller in a feedback loop to confirm accuracy, is calculated as a function of a constant CPAP prescription pressure and a proportional value of patient flow. A relief or augmentation constant defines the degree thereof, and the patient flow is estimated. The value of the constant is zero during inspiration, thus providing no pressure augmentation and the delivered pressure is equivalent to the base or prescription pressure. During expiration, the value of the constant is non-zero, and the pressure delivered to the patient is the prescription pressure less a proportional amount of the estimated instantaneous patient flow. A signal representative of the delivered pressure drives the blower hardware delivering therapeutic air flow to the patient. Although the method disclosed by Estes, et al., allows the delivered therapeutic pressure to the patient to be tuned to a greater degree, the patient nevertheless experiences discomfort.

Another approach to the issue of excess pressure at the expiration stage is disclosed in U.S. Pat. No. 7,128,069 to Farrugia et al. When a transition from the inspiration phase to the expiration phase is detected, i.e., when the pressure at the patient's mouth begins to drop, the motor that controls the blower is understood to be de-energized and allowed to freewheel. After the pressure increases back to a predetermined level, which in the Farrugia et al. disclosure is 3 cm $H_2O$, the blower motor is restarted to bring the pressure at the patient's mouth to prescription levels (10 cm $H_2O$). Thus, the temporary stopping of the blower is understood to function as a pressure relief during expiration. However, due to the wind-up and wind-down times associated with starting and stopping an electrical motor, patient comfort is not optimized due to the existence of residual pressure.

Accordingly, there is a need in the art for improved methods and systems for continuous positive airway pressure (CPAP) therapy including the use dual pressure sensors at a source and on a ventilation mask to control an exhalation valve.

BRIEF SUMMARY OF THE INVENTION

In accordance with various embodiments of the present disclosure, a respiratory assistance device is contemplated. The device may include a variable speed blower with an output, as well as a patient ventilation interface configured for fitment on a patient respiratory passageway. The patient ventilation interface may include a piloted exhalation valve. Furthermore, the device may include a gas passage conduit that can couple the output of the blower to the patient ventilation interface. A pilot line from the gas passage conduit may be coupled to the pilot of the exhalation valve. There may be a pressure sensor that measures a mask pressure in the patient ventilation interface, and a blower speed sensor that measures a speed of the blower. The device may further include a pressure controller that is in communication with the pressure sensor and the blower speed sensor. A patient inspiratory phase and a patient expiratory phase may be detectable from at least one of the measured speed of the blower and a set speed of the blower. The pressure controller can adjust an operating speed of the blower and actuate the piloted exhalation valve based upon the measured mask pressure.

According to another embodiment, a continuous positive airway pressure (CPAP) apparatus for respiratory assistance of a patient is disclosed. The apparatus may include a blower with an output connectible to a ventilation mask wearable by the patient. The blower may have a variable speed. There may also be a pressure sensor that is connected to the ventilation mask for measuring mask pressure therein, and a blower speed sensor connected to the blower for measuring the variable speed of the blower. The apparatus may include a blower controller that is connected to the pressure sensor and the blower speed sensor. A patient inspiratory phase and a patient expiratory phase may be detectable from at least one of the measured speed of the blower and a set speed of the blower to set a therapeutic pressure at the patient.

Yet another embodiment of the present disclosure contemplates a method for administering continuous positive airway pressure (CPAP) therapy to a patient. The method may include a step of receiving a first CPAP therapeutic pressure value. There may also be a step of measuring a blower speed from the blower that is generating therapeutic pressure to the patient, as well as a step of measuring a mask pressure value at a ventilation mask worn by the patient. The method may include evaluating a patient respiratory state from the blower speed. The patient respiratory state may be one of an inspiration state and an expiration state. Furthermore, there may be a step of selectively adjusting the blower speed to deliver the therapeutic pressure to the patient in response to the evaluated patient respiratory state. The speed of the blower may generate a quantity of the therapeutic pressure corresponding to the first CPAP therapeutic pressure value.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which.

Common reference numerals are used throughout the drawings and the detailed description to indicate the same elements.

DETAILED DESCRIPTION OF THE INVENTION

The detailed description set forth below in connection with the appended drawings is intended as a description of the several presently contemplated embodiments of a system for continuous positive airway pressure (CPAP) therapy. The system delivers breathing gas to a patient for the treatment of obstructive sleep apnea (OSA) and other cardio-pulmonary conditions, and implements various methods for the selective pressure augmentation and relief throughout the breathing cycle. This description is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
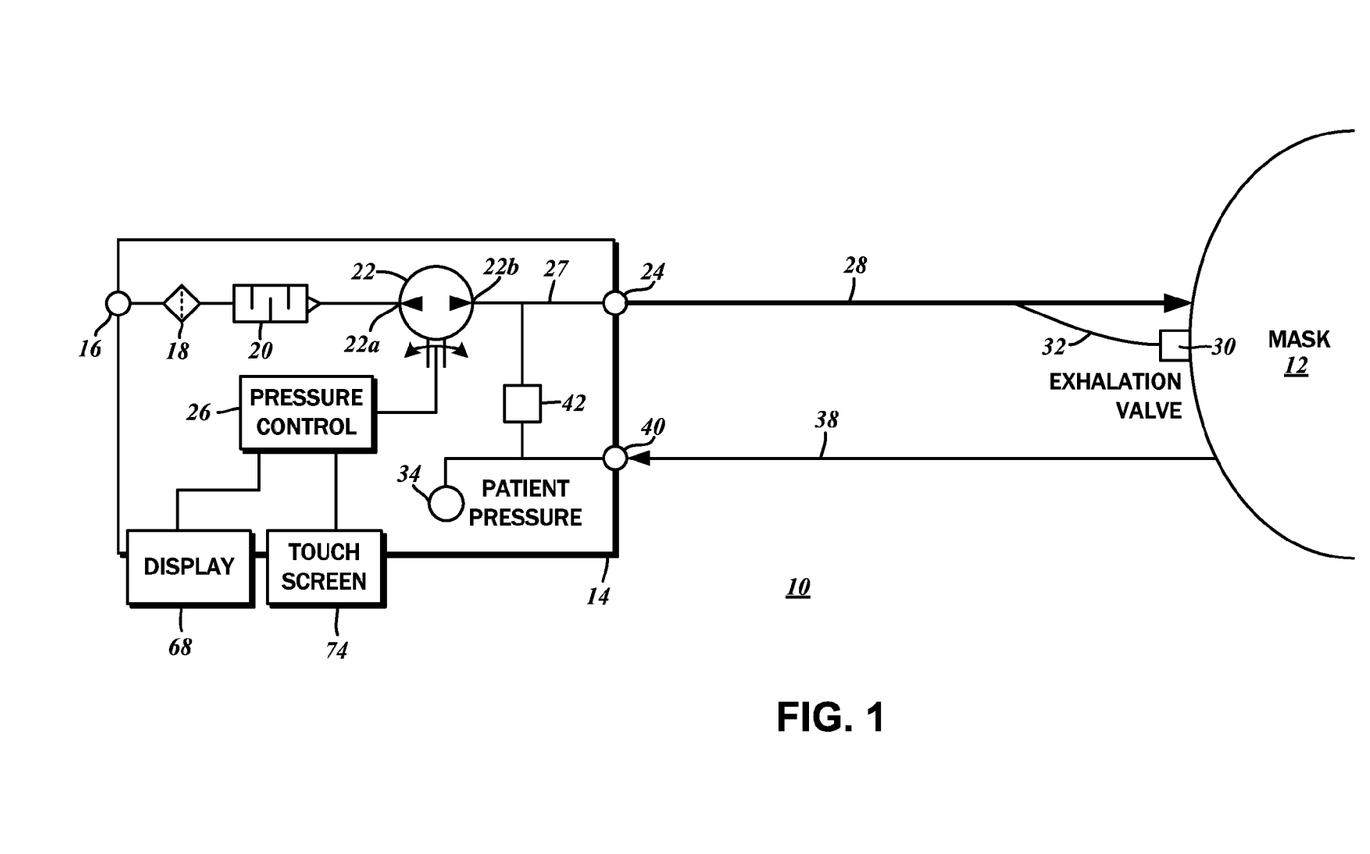
FIG. 1 is a block diagram showing the various components of a CPAP apparatus in accordance with various embodiments of the present disclosure including a ventilation unit, a patient ventilation mask, and gas passage conduits.

With reference to the block diagram of FIG. 1, one embodiment of the present disclosure contemplates a CPAP system 10 generally comprised of a patient ventilation interface 12 and a ventilation unit 14. The patient ventilation interface 12 may include such devices as a full-face mask or a nasal mask that can be placed in direct gas flow communication with the upper respiratory tract of the patient, i.e., the nasal cavity and the oral cavity. One embodiment of the CPAP system 10 may utilize a nasal mask such as that described in U.S. patent application Ser. No. 13/411,348 entitled VENTILATION MASK WITH INTEGRATED PILOTED EXHALATION VALVE filed Mar. 2, 2012, now issued U.S. Pat. No. 8,844,533, and U.S. patent application Ser. No. 13/411,407 entitled VENTILATION MASK WITH INTEGRATED PILOTED EXHALATION VALVE filed Mar. 2, 2012, now issued U.S. Pat. No. 8,839,791, the disclosures of which are hereby incorporated by reference in their entireties herein. It will be appreciated that other apparatuses that so interface the respiratory system of the patient to the ventilation unit 14 may be substituted without departing from the scope of the present disclosure, so long as certain features noted below are incorporated.

Generally, the ventilation unit 14 generates a flow of breathing gas that is delivered to the patient via the patient ventilation interface 12. The breathing gas may be ambient air, a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a ventilation source 22. There is an inlet port 22a coupled to the sound suppressor 20, and an outlet port 22b that is in gas flow communication with an outlet port 24 of the ventilation unit 14. It will be recognized that any suitable ventilation source 22 capable of generating the gas flow and pressure suitable for CPAP treatment in accordance with the present disclosure may be utilized, including centrifugal fans and other like blowers. The ventilation source 22 is driven electrically and its actuation is governed by a programmable controller 26, which implements the various methods of CPAP treatment contemplated by the present disclosure as will be described in further detail below.

The flow of breathing gas that is output from the ventilation source 22 is passed through the outlet port 24 to a gas conduit 28 that is in coupled to the aforementioned mask or patient ventilation interface 12. The gas conduit 28 is understood to be a plastic tube having a predetermined inner diameter such as 22 mm or smaller, though any other conduit of suitable material and construction may be utilized. The patient ventilation interface 12 in accordance with various embodiments of the present disclosure also includes a piloted exhalation valve 30 that is selectively actuated depending on the pressure differential between the patient ventilation interface 12 and the ventilation unit 14. The exhalation valve 30 is connected to a pilot line 32 that branches from the gas conduit 28. A pressure difference is generated between the patient ventilation interface and the exhalation valve, such that it is closed during inspiration and opened during expiration.

As will be explained in further detail below, detection of the inspiration and expiration is contemplated to be a function of the pressure at the patient ventilation interface and the speed of the ventilation source 22. In order to read the pressure at the ventilation interface, the presently contemplated CPAP system 10 includes a mask or patient interface pressure sensor 34. The patient interface pressure sensor 34 is physically disposed within the ventilation unit 14, but is in direct gas flow communication with the mask or patient ventilation interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 38. This can be done through a purge solenoid 42 connected to both. The purge can be continuous or intermittent according to the patient's breathing phase or pressure difference between the blower pressure and the mask pressure.

Figure 2:
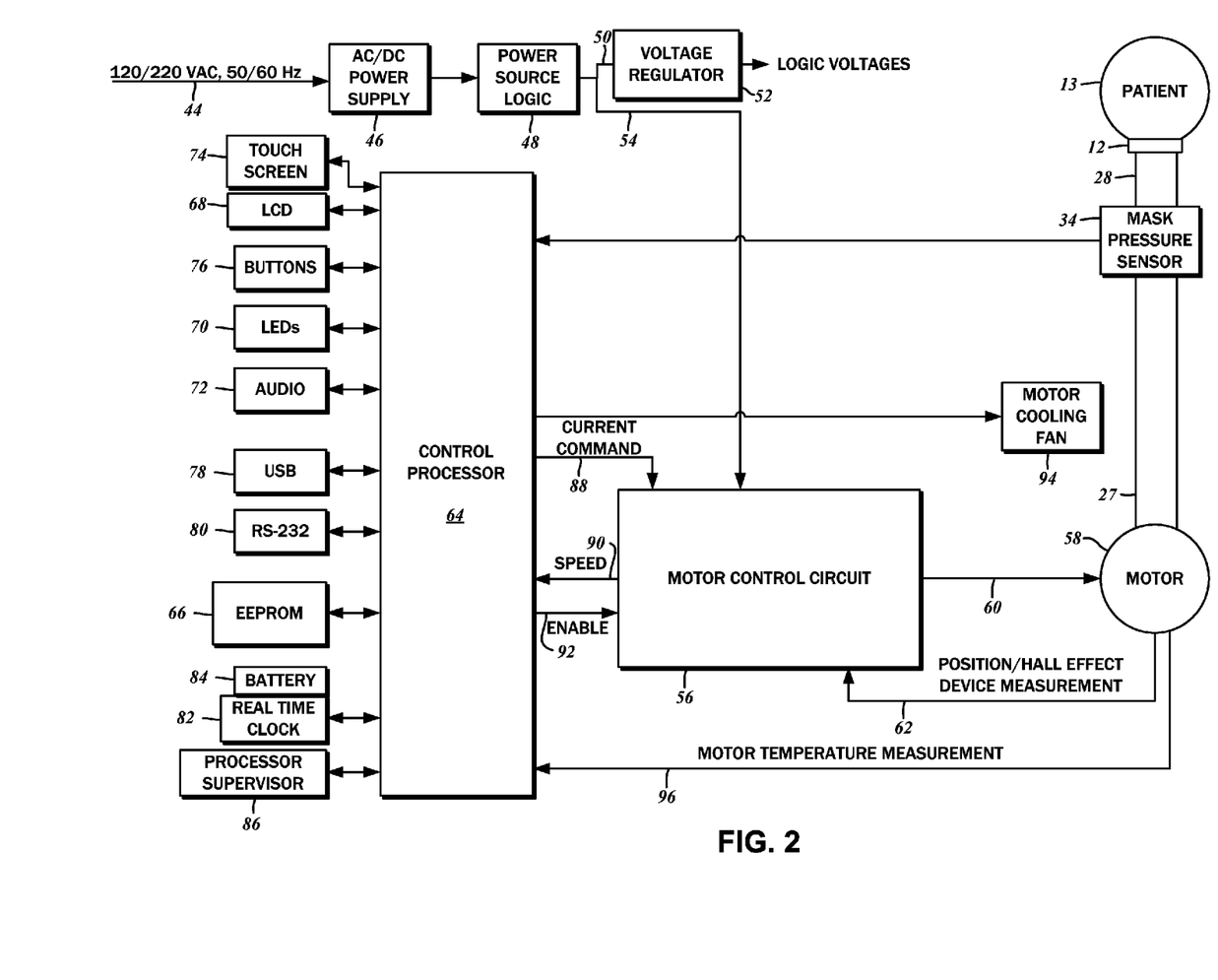
FIG. 2 is a block diagram illustrating the electrical components of the ventilation unit.

The block diagram of FIG. 2 illustrates the various electrical components of one typical embodiment of the ventilation unit 14. Power for the ventilation unit 14 may be provided from a conventional household electricity supply of either 120V or 220V alternating current (AC), at 50 Hz or 60 Hz. The block diagram denotes this supply as a power source 44. A power supply 46 is connected to the power source 44, and as will be recognized by those having ordinary skill in the art, the power signal is variously rectified, filtered, and stepped down to a direct current (DC) voltage. In accordance with one embodiment of the present disclosure, the DC voltage source is 24 V. It is understood that the ventilation source 22 utilizes a higher DC voltage than control logic devices, and thus the power supply 46 is connected to a power source logic 48. A first output 50 of the power source logic 48 is connected to an integrated circuit voltage regulator 52 that steps down the DC voltage to the logic device level of 5V. A second output 54 of the power source logic 38 is the existing high DC voltage directly from the power supply 46, and is connected to a motor control circuit 56.

The ventilation source 22 is comprised of several electrical components, including a motor 58 and the aforementioned motor control circuit 56. In accordance with one embodiment, the motor 58 is a brushless DC or electrically commutated motor. It will be recognized that the speed of rotation of the motor 58 is based upon input logic signals provided to the motor control circuit 56, which drives electrical current through its windings that induce magnetic fields that translate to rotational motion of the attached rotor. A fan coupled to the rotor thus rotates and generates a flow of air through an internal conduit 27. The internal conduit 27 is coupled to the outlet port 24, which is coupled to the gas conduit 28. As described above, the patient interface pressure sensor 34 is connected to the pneumatic circuit between the motor 58 and the patient 13.

The motor control circuit 56 has a motor drive output 60 that is connected to the motor 58. The rotational position of the motor 58 is detected by a Hall-effect sensor that is incorporated into the motor 58. An output voltage 62 from the Hall-effect sensor is fed back to the motor control circuit 56, which ensures that the actual position corresponds to the intended or commanded position.

The controller 26 and its functionality may be implemented with a programmable integrated circuit device such as a microcontroller or control processor 64. Broadly, the control processor 64 receives certain inputs, and based upon those inputs, generates certain outputs. The specific operations that are performed on the inputs may be programmed as instructions that are executed by the control processor 64. In this regard, the control processor 64 may include an arithmetic/logic unit (ALU), various registers, and input/output ports. Although external memory such as EEPROM (electrically erasable/programmable read only memory) 66 may be connected to the control processor 64 for permanent storage and retrieval of program instructions, there may also be an internal random access memory (RAM). One embodiment contemplates the use of an Intel 8081 instruction set/architecture, though any other suitable instruction set or processor architecture may be substituted. As indicated above, the control processor 64 is powered by a low voltage DC supply from the voltage regulator 54.

As mentioned above, in order to set the operational parameters of the ventilation unit 14, and to initiate or terminate certain functions, a graphical user interface is provided. Such graphical user interface is generated on a display screen 68, which may be of a liquid crystal display (LCD) type. Any type of graphic may be shown on the display screen 68, though for more specific indicators, a simple light emitting diode (LED) device 70 may be utilized. It will be recognized that alarm conditions, power status, and the like may be indicated with the LED device 70. Audible outputs may also be produced with audio transducers 72 that are likewise connected to the control processor 64. Among the contemplated outputs that may be generated on the audio transducer 72 include simple beeps and alarms, as well as sophisticated voice prompts that provide information and instructions.

An operator may interact with the graphical user interface through different input devices such as a touch screen interface 74 that is overlaid on the display screen 68. It will be recognized that various graphic elements may be generated on the display screen 68, with touch inputs/interactions corresponding in position to those graphic elements being evaluated as a selection or activation of the same. Various touch screen interfaces, some of which may be directly integrated with the display screen 68, are known in the art. Besides touch screen inputs, buttons 76 may also be connected to the control processor 64 for similarly receiving user inputs. It is understood that the audio transducer 72 may also accept sound input in the form of voice commands, the processing of which is performed may be performed by the control processor 64.

Several modalities for connecting to and communicating with other data processing devices such as general-purpose computers are also contemplated. Accordingly, the control processor 64 may be connected to a universal serial bus (USB) controller 78. For more basic communications, there may be a serial RS-232 transceiver 80. Through these data communications modalities, the configuration options of the ventilation unit 14 may be set, operating profiles may be downloaded, and so forth. Notwithstanding the specific reference to USB and RS-232 communications modalities, any other communications modality including wireless systems may be substituted without departing from the present disclosure.

The functions of the ventilation unit 14 depend on proper synchronization, and so the control processor 70 is connected to a real time clock 82 that maintains a common clock cycle. Although a primary feature of the real time clock 82 is to maintain synchrony at a processor cycle level, longer term time data is also maintained. In order to retain such time data, the real time clock 82 may be powered independently of the primary power source 44, and there is accordingly a battery backup 84. Under heavy processing loads or unexpected program conditions, the control processor 64 may become unable to execute critical programmed steps in real-time. Thus, the control processor 64 may include a processor supervisor 86 that invokes a program execution break upon detecting such conditions. Typically, this is implemented as a step of clearing a memory variable periodically, and when that step is unable to take place because instruction execution is frozen or otherwise delayed, the processor supervisor 86 may cause a predetermined routine to be executed.

As mentioned above, the motor 58 is driven by the motor control circuit 56, which generates different outputs depending on signals received from the control processor 64. The signal to drive the motor 58 is generated on a current command line 88. For control processing on a broader level, feedback from the ventilation source 22 is utilized, and in the specific form of a speed or current measurement input 90 from the motor control circuit 56. Furthermore, as detailed below, pressure readings at the patient 13 is utilized to reach control decisions. Accordingly, the patient interface pressure sensor 34 is connected to the control processor 64. The ventilation source 22 is activated and deactivated via a motor enable line 92. To ensure that the temperature of the motor 58 remains within operational parameters, a motor cooling fan 94 may be driven directly by the control processor 64. In some embodiments, there may be additional control circuitry that isolates the power source of the motor cooling fan 94 from the control processor 64. The decision to activate and deactivate the motor cooling fan 94 may be made in response to temperature readings from the motor 58, and so there is a motor temperature reading 96 passed to the control processor 64.

Figure 3:
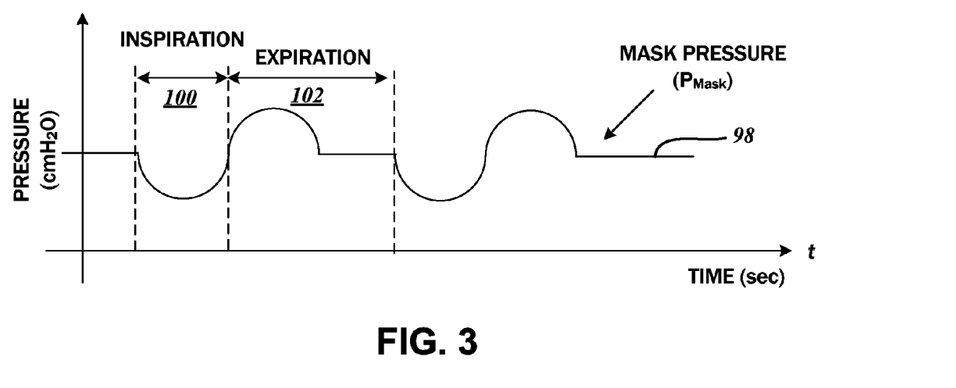
FIG. 3 is a graph illustrating the pressure cycles at the patient mask over a typical breathing sequence including inspiratory phases and expiratory phases.

Referring now to the pressure diagram of FIG. 3, a first plot 98 illustrates the pressure cycle at the patient ventilation interface 12, and is characterized by an inspiration region 100 and an expiration region 102. As will be appreciated, pressure at the patient ventilation interface 12 decreases during inspiration, and increases during expiration. Henceforth, the first plot 98 and the measurement represented thereby will be referred to as $P_{Mask}$, with the pressure value at any particular time t being referred to as $P_{Mask}(t)$. This pressure is given in terms of $cmH_2O$, as are the other pressure measurements discussed herein.

Figure 4:
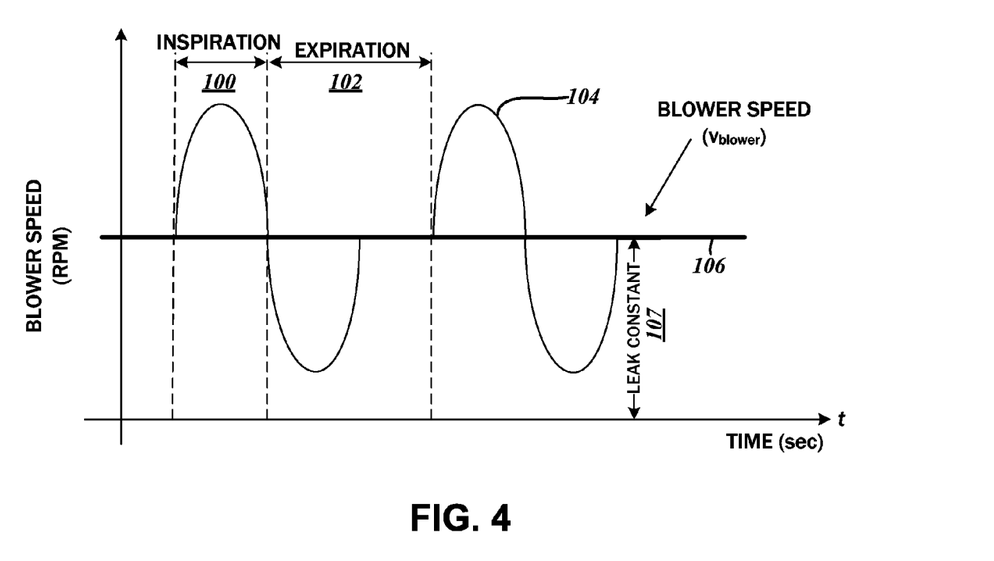
FIG. 4 is a graph plotting the operating speed of a ventilation source over the typical breathing sequence in accordance with various embodiments of the present disclosure.

As shown in the diagram of FIG. 4, the operating speed of the ventilation source 22, on the other hand, is understood to exhibit an opposite response as shown by a second plot 104. The blower operating speed increases during the inspiration region 100 and decreases in the expiration region 102. The second plot 104 and the measurement represented thereby will be referred to as $V_{Blower}$, with the pressure value at any particular time t being referred to as $P_{Blower}(t)$. As can be seen, the operating speed of the ventilation source 22 exhibits a generally a reciprocal relationship with respect to the pressure at the patient ventilation interface 12. That is, when $P_{Mask}$ peaks, $V_{Blower}$ is at its lowest, and vice versa.

In accordance with various embodiments of the present disclosure, the indication of leakage at the patient ventilation interface 12 is contemplated. As further shown in the graph of FIG. 4, the second plot 104 has an average value 106, which corresponds to a leak constant 107. Generally, the greater the average operating speed of the ventilation source 22, the greater the leakage, and this relationship serves as a basis for the quantified comparisons that define the degree of leakage.

As referenced herein, the terms patient ventilation interface 12 and patient mask are utilized interchangeably. It will be recognized that the patient mask is a specific kind of patient ventilation interface, and as explained briefly above, other types of ventilation interfaces may be utilized. Along these lines, reference to such terms as mask pressure, blower speed, or the use of the term mask or blower to modify any other term is for purposes of convenience only and not of limitation. For instance, mask pressure is understood to refer to the pressure in the patient ventilation interface 12, while blower pressure refers to the pressure at the output of the blower 22.

Figure 5:
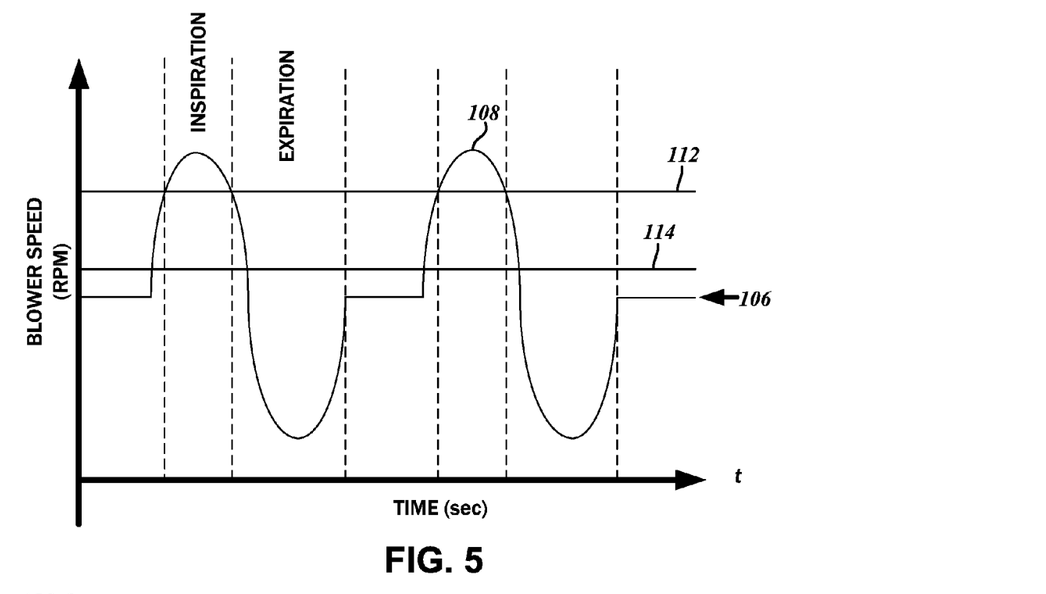
FIG. 5 is a graph plotting the operating speed of the ventilation source with a superimposed threshold that defines when triggering and cycling occur.

Referring now the graph of FIG. 5, the determination of the patient trigger and cycle states will now be considered. It is understood that cycling and trigger states are based on the patient's breathing cycle, and so the present disclosure contemplates a modality by which the inspiration phase and the expiration phase can be ascertained. A plot 108 represents the blower speed $V_{Blower}$ over a time period t.

It is contemplated that the ventilation source 22 is operated in the linear region, that is, the operating speed of the ventilation source 22 pressure directly corresponds to the pressure generated thereby. Certain embodiments envision pressure differentials to be induced between the ventilation source 22 and the patient ventilation interface 12. However, because of the direction relationship between the pressure the speed, any evaluations for determining inhalation and exhalation state can be substituted with the speed of the ventilation source 22. The particular configuration of the CPAP system 10 in which minimal air flow rates are required is understood to make possible operating the ventilation source 22 in its linear region.

Figure 6:
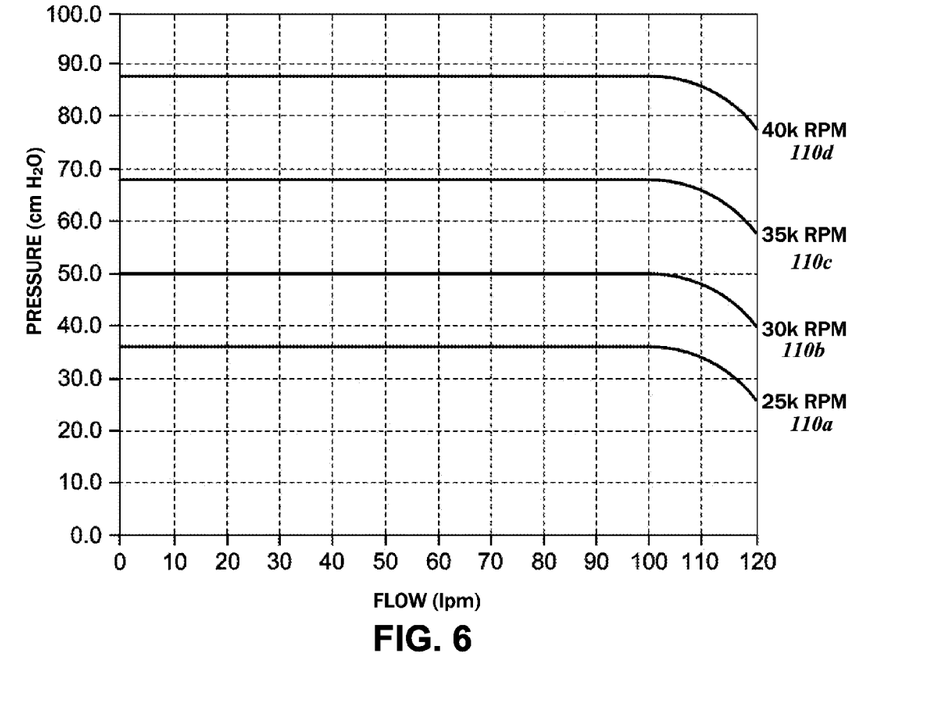
FIG. 6 is a graph plotting the generated pressure and flow rate for a series of operating speeds of the ventilation source.

Referring briefly to the graph of FIG. 6, there are a series of plots 110 that represents the pressure generated (cm $H_2O$) at differing operating speeds. More particularly, a first plot 110*a* represents the generated pressure for an operating speed of 25,000 rpm. As shown, the pressure remains constant for low flow rates up to around 100 lpm, after which drastic reductions in pressure occur. The same is true for an operating speed of 30,000 rpm shown in a second plot 110*b*, which maintains a generated pressure of around 50 cm $H_2O$ in its linear region, as well as an operating speed of 35,000 rpm shown in a third plot 110*c*. Here, a pressure of around 68 cm $H_2O$ is exhibited in the linear region. For an operating speed of 40,000 rpm as shown in a fourth plot 110*d*, the pressure is around 88 cm $H_2O$.

The illustrated blower operating speeds shown in the plots 110 are presented by way of example only and not of limitation, and the ventilation source 22 can be operated in any intermediate speed. Along these lines the foregoing operating characteristics of the ventilation source 22 are also exemplary only. It is to be understood that different variants of the ventilation source 22 may have different operating characteristics, and those having ordinary skill in the art will recognize the needed accommodating modifications.

With reference back to the graph of FIG. 5, in accordance with one embodiment, a trigger limit 112 is set or otherwise computed as an average of the blower operating speed. More particularly, the trigger limit 112 at time (t) may be the average blower operating speed also at time (t) plus a predetermined trigger constant, which may be set by the clinician or the patient. If the blower operating speed at (t) is greater than the trigger limit at the same time (t), the patient is considered to be in the inspiration phase.

A cycle limit 114 is also set, and is understood to be a function of the peak value of the operating speed. In further detail, the cycle limit at time (t) is the maximum operating speed at time (t) multiplied by a cycle constant. The cycle constant can also be set by the clinician or the patient, or otherwise computed as a function of the operating speed. If the operating speed is less than the set cycle limit, then the patient is determined to be in the expiration phase.

Figure 7:
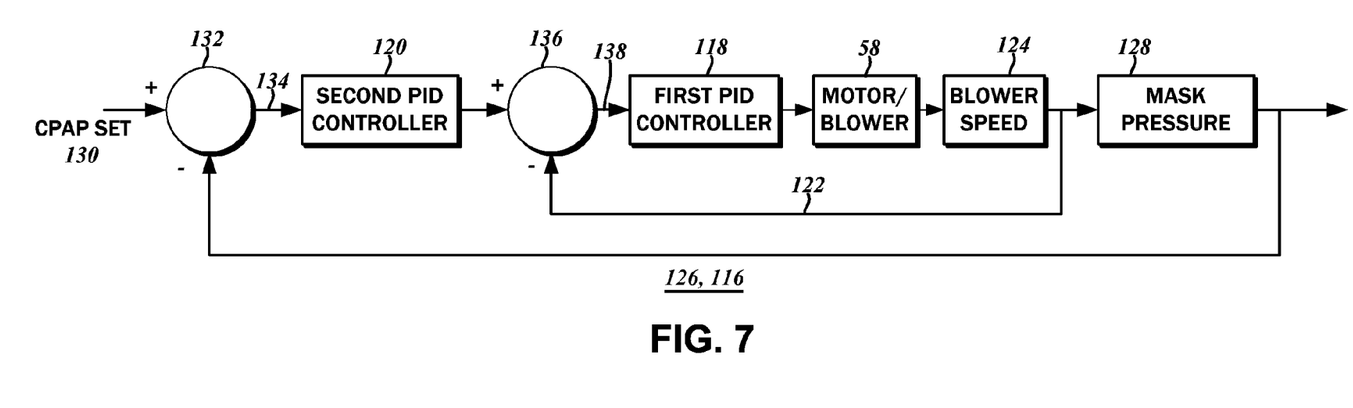
FIG. 7 is a control loop block diagram depicting pressure sensor and speed corresponding to the blower speed and a mask pressure as inputs to control devices.

The specific pressure that is to be delivered to the patient by way of the ventilation source 22 is set by the programmable controller 26, and FIG. 7 is a control loop block diagram thereof. The piloted exhalation valve 30 further provides pressure relief depending on the current pressure difference between the ventilation source 22 and the patient ventilation interface 12, the details pertaining to the operation of which will be discussed more fully below. The exhalation valve 30 is configured to open to ambient pressure when the pressure difference (ΔP) is small or negative, and closes when pressure difference (ΔP) is sufficiently high.

Still referring to the control loop block diagram of FIG. 7, additional details pertaining to the motor control functions of the ventilation source 22, and specifically the closed loop control circuit 116, will now be considered. Generally, the closed loop control circuit 116 includes a first PID controller 118, and a second PID controller 120, both of which act upon the motor 58 to effectuate pressure changes within the patient circuit. There is a first or inner control loop 122 that is driven by the first PID controller 118 to modulate the speed of the motor 58 and thus a blower speed/operating speed 124, as well as a second or outer control loop 126. Together with the first PID controller 118 and the second PID controller 120, mask pressure 128 is modulated. The inner control loop 122 and the outer control loop 126 are inter-related and together define the closed loop control circuit 116.

One objective of the closed loop control circuit 116 is to operate the ventilation source 22 to the extent necessary to achieve a predetermined pressure sufficient to meet the inspiratory pressure demands of the patient and the pressure losses in the ventilation system 14. A desired pressure, which is the preset CPAP pressure as input by the clinician, is represented by an input value 130 that is provided to a first summing point 132. The pressure at the patient ventilation interface 12, i.e., mask pressure 128, is measured by pressure sensor as discussed above, and also input to the first summing point 132. An output signal 134 corresponding to the summed pressures of the input value 130 and the mask pressure 128 is passed to the second PID controller 70. The output signal 134 is processed by the second PID controller 120, and this processed signal is output to the motor control circuit 56 to partially regulate the ventilation source 22 in response.

The output from the second PID controller 120 is input to a second summing point 136, which also adds the operating speed of the blower, i.e., the ventilation source operating speed 124. Another output signal 138 corresponding to these summed values is passed to the first PID controller 118, which again is processed and output to the motor control circuit 56 to regulate the ventilation source 22. The subsequent blower operating speed sensor 124 measurement is again fed back to the second summing point 136, at which point the inner loop continues.

The first PID controller 118 is thus part of a closed loop control over a ventilation source speed sensor 124, with the output thereof being the current set point for the ventilation source 22. Furthermore, the second PID controller 120 minimizes the error between the mask pressure and the CPAP set level 130. The output of the second PID controller 120 is the set pressure for the first PID controller 118. The respective gains of the first PID controller 118 and the second PID controller 120 may be scheduled according to the patient breathing phase and/or the CPAP set level 130. During expiration, the programmable controller 26 can be reconfigured to control the speed of the ventilation source 22, blower pressure, blower flow, either alone or to different set targets. Upon detecting an inspiration phase, the CPAP set level 130 can be set to a different value than during expiration, a technique known as Bi-level CPAP.

Figure 8:
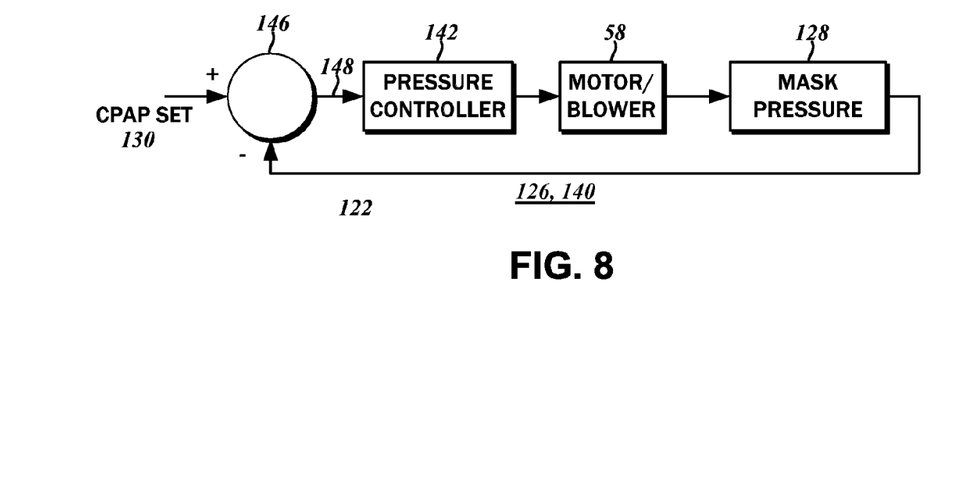
FIG. 8 is another control loop block diagram showing a closed-loop controller for mask pressure.

With reference to FIG. 8, the present disclosure contemplates another closed loop control circuit 140 to confirm the delivery of the specified CPAP pressure 130 to the patient ventilation interface 12. In further detail, the closed loop control circuit 140 includes a pressure controller 142 that generally corresponds to the programmable controller 26. The pressure controller 142 acts upon the motor 58 to effectuate pressure changes within the patient circuit, and a mask pressure 28 is applied. The pressure at the patient ventilation interface 12, i.e., mask pressure 128, which is measured by the pressure sensor 34, is input to a summing point 146 and compared against the specified CPAP pressure 130. An output 148 of the summing point 146 in turn serves as the control input for the pressure controller 142.

Figure 9:
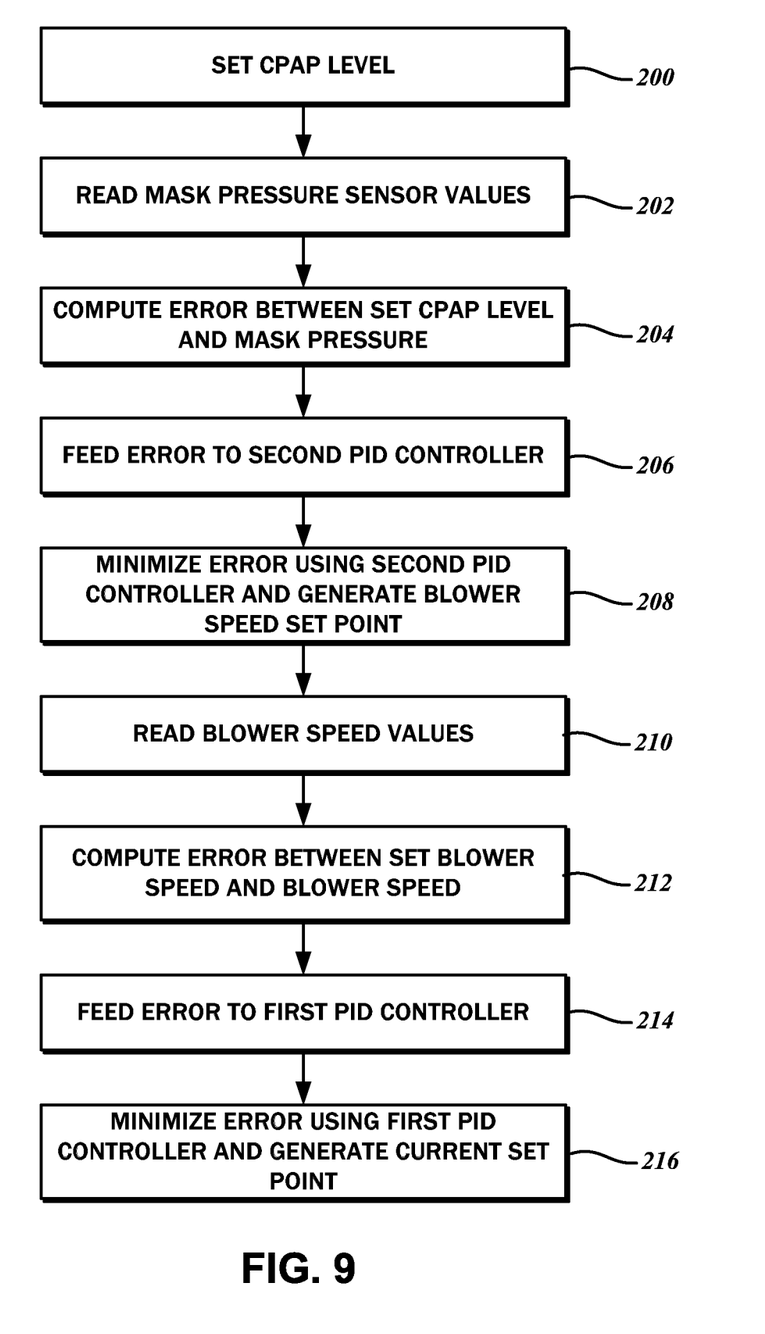
FIG. 9 is a flowchart illustrating the processing steps of the control loop shown in FIG. 7.

With reference to the flowchart of FIG. 9, the steps involved in the control loop circuit 116 will be described. In a step 200, the CPAP level 73 is set. The mask pressure 128 is then read in a step 202, and the error between the set CPAP level 130 and the mask pressure 128 is computed in a step 204, as described above in relation to the second summing point 136. In a step 206, the computed error is fed to the second PID controller 120. The ventilation source 22 is modulated by the second PID controller 120 in a step 208 to minimize the error between the set CPAP level 130 and the mask pressure 128. At this point, the blower operating speed set point is generated. Per the inner control loop 122, the blower operating speed sensor 124 measurement is received in a step 210, and an error between such value and the blower operating speed set point from the second PID controller 120 is computed in a step 212. The amount of error is then fed to the first PID controller 118 in accordance with a step 214. The error is minimized by further modulating the ventilation source 22 in a step 216, thereby generating the current set point.

Figure 10:
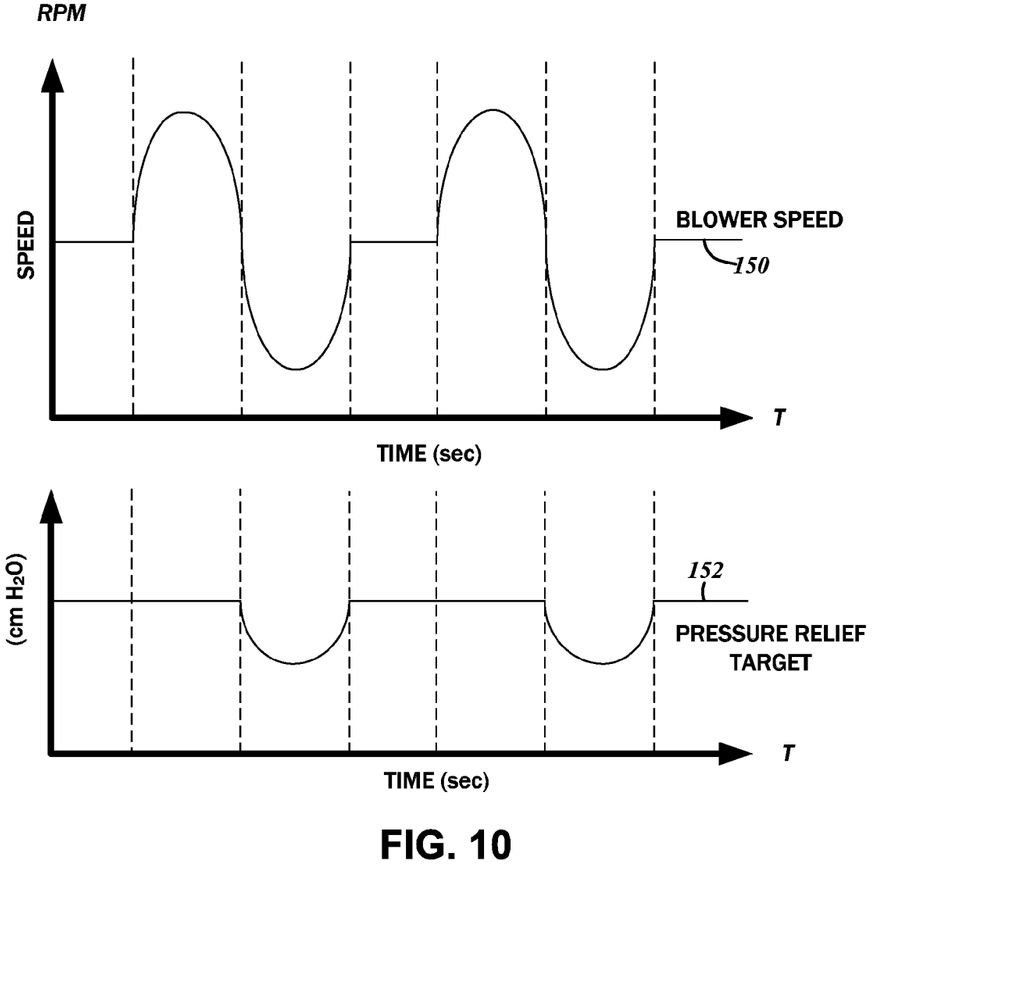
FIG. 10 is a graph showing the operating speed of the ventilation source and a corresponding pressure relief target.

The pressure relief target is understood to be a function of the blower operating speed. The pressure diagram of FIG. 10 includes a plot 150 of the speed $V_{Blower}(t)$ over a breathing cycle. During the time the instantaneous blower operating speed is lower than average, the mask pressure target is also reduced to create a pressure relief 152. For improved patient comfort, pressure at the patient could be further reduced according to a function of the blower operating speed. The target mask pressure at time (t) is contemplated to be the set CPAP level 130 during the inspiration phase. During the expiration phase, the target pressure at time (t) is contemplated to be the set CPAP level 130 reduced by a function of the blower operating speed $V_{Blower}(t)$ multiplied by a relief constant. The relief constant and a minimum mask pressure level may also be set.

Figure 11:
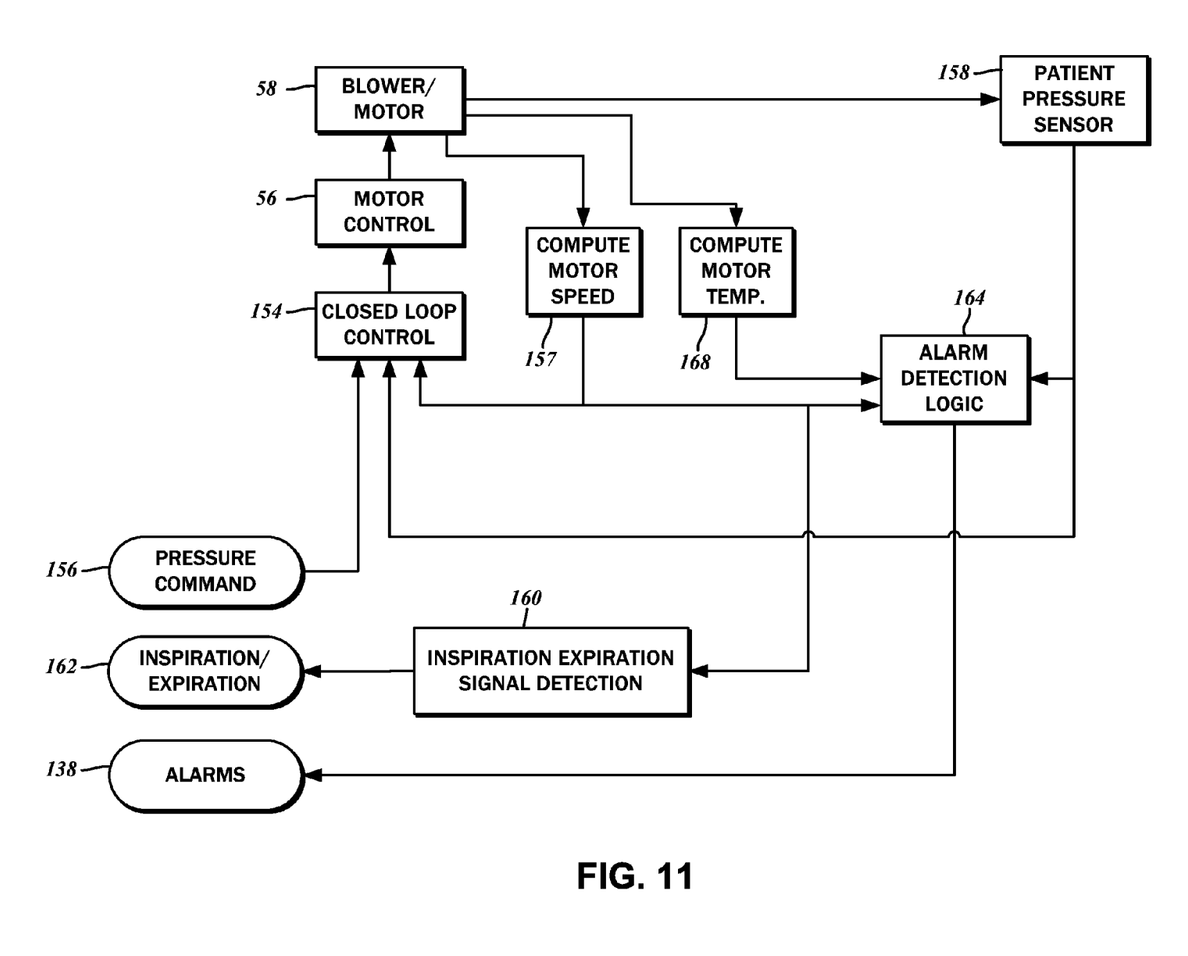
FIG. 11 is a block flow diagram showing the interrelated components of the ventilation unit.

With reference to the flow diagram of FIG. 11, the operational sequence of the CPAP system 10 will be considered. As indicated above, the motor 58 is driven by a motor control circuit 56, that is, electrical current is selectively applied by the motor control circuit 56 to the conductive elements of the motor 58 to induce a magnetic field that produces rotation. The specific sequence and manner in which the ventilation source 22 (i.e., the motor 58 and the motor control circuit 56) is actuated is governed by a closed loop control circuit 154 that is implemented by the programmable controller 26. One of the inputs to the closed loop control circuit 154 is a pressure command 156, or the therapeutic pressure that is set by a clinician.

An actuation of the motor 58 changes its speed. This is sensed in a speed sensor block 157. Furthermore, pressure readings are also made at the patient ventilation interface 12, or a mask pressure sensor block 158. These readings are inputs to the closed loop control circuit 154. Additionally, the readings from the speed sensor block 157 are utilized in a breathing cycle state detector block 132. As mentioned above, the blower operating speed can be utilized to determine whether the patient 13 is in an expiration (exhalation) state or an inspiration (inhalation) state. The breathing cycle state detector 160 so utilizes the speed measurements and generates a breathing cycle state output 162.

Different alarm conditions may be evaluated based in part on the pressure measurements from the mask pressure sensor block 158. These values are passed to an alarm detection logic block 164 that can trigger an alarm 166. Besides the pressure measurements, the speed of the motor 88 calculated in the speed sensor block 157, and the temperature of the same as calculated in a motor temperature sensor block 168. These calculated values are also passed to the alarm detection logic block 164. Referring back to the block diagram of FIG. 2, the performance of the motor 58 can be adjusted according to its temperature. The command being passed from the control processor 64 to the motor control circuit 56 may be a function of a temperature reading from the motor temperature sensor block 168. More specifically, the maximum current applied to the motor 58 can be a function of the motor temperature reading.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present invention with more particularity than is necessary, the description taken with the drawings making apparent to those skilled in the art how the several forms of the present invention may be embodied in practice.

What is claimed is:

1. A respiratory assistance device, comprising:
   a variable speed blower with an output;
   a patient ventilation interface configured for fitment on a patient respiratory passageway, the patient ventilation interface including a ventilation mask and a piloted exhalation valve coupled to the ventilation mask;
   a gas passage conduit coupling the output of the blower to the patient ventilation interface, a pilot line from the gas passage conduit being coupled to the pilot of the exhalation valve;
   a pressure sensor for measuring a mask pressure in the patient ventilation interface;
   a blower speed sensor for measuring a speed of the blower; and
   a pressure controller, in communication with the pressure sensor and the blower speed sensor, that detects a patient inspiratory phase and a patient expiratory phase based on either or both of the measured speed of the blower and a set speed of the blower, the pressure controller adjusting an operating speed of the blower and actuating the piloted exhalation valve by selective application of fluid pressure to the pilot line from the gas passage conduit based upon the measured mask pressure.

2. The respiratory assistance device of claim 1, wherein the pressure controller actuates the blower to induce a pressure differential at the patient ventilation interface and the blower that closes the piloted exhalation valve during the patient inspiratory phase and opens the piloted exhalation valve during the patient expiratory phase.

3. The respiratory assistance device of claim 2, wherein the piloted exhalation valve is open to ambient pressure with the pressure differential being lower than a predefined threshold.

4. The respiratory assistance device of claim 2, wherein the piloted exhalation valve is open to ambient pressure with the pressure differential being approximately zero to negative.

5. The respiratory assistance device of claim 4, wherein the piloted exhalation valve is closed with the pressure differential being higher relative to the pressure differential of when the piloted exhalation valve is open.

6. The respiratory assistance device of claim 1, wherein the pressure controller regulates therapeutic pressure at the patient ventilation interface according to a trigger limit and a cycle limit using the blower speed.

7. The respiratory assistance device of claim 6, wherein an average blower speed over one or more patient breathing cycles defines a leak constant.

8. The respiratory assistance device of claim 7, wherein the trigger limit is defined by the leak constant added to a trigger constant.

9. The respiratory assistance device of claim 6, wherein the cycle limit is defined by a cycle constant fraction of a maximum blower speed.

10. The respiratory assistance device of claim 1, wherein the pressure controller relieves mask pressure by reducing therapeutic pressure at the patient, the therapeutic pressure being a function of the blower speed.

11. The respiratory assistance device of claim 1, wherein the pressure controller includes a first proportional-integral-derivative (PID) controller and a second proportional-integral-derivative (PID) controller, the first PID controller being part of a first control loop over the speed of the blower for minimizing error between the set speed of the blower and the measured speed of the blower, and the second PID controller, together within the first control loop, being part of a second control loop for minimizing error between the mask pressure and a set pressure.

12. The respiratory assistance device of claim 1, further comprising:
a temperature sensor for a motor of the blower;
wherein a particular speed at which the motor is driven by the pressure controller to regulate a blower speed corresponding to delivered therapeutic pressure is a function of temperature readings from the temperature sensor.

13. A continuous positive airway pressure (CPAP) apparatus for respiratory assistance of a patient, the apparatus comprising:
a blower with an output connectible to a patient ventilation interface including a ventilation mask wearable by the patient and a piloted exhalation valve coupled to the ventilation mask, the blower having a variable speed;
a pressure sensor connected to the ventilation mask for measuring mask pressure therein;
a blower speed sensor connected to the blower for measuring the variable speed of the blower; and
a blower controller connected to the pressure sensor and the blower speed sensor, a patient inspiratory phase and a patient expiratory phase being detectable from at least one of the measured speed of the blower and a set speed of the blower to set a therapeutic pressure at the patient;
wherein the piloted exhalation valve is opened and closed by selective application of fluid pressure thereto based upon the pressure differentials between the mask pressure and a blower pressure induced by the blower controller driving the blower.

14. The respiratory assistance device of claim 13, wherein the piloted exhalation valve is open to ambient pressure with the pressure differential being low lower than a predefined threshold.

15. The CPAP apparatus of claim 13, wherein the piloted exhalation valve is open to ambient pressure with the pressure differential being approximately zero to negative.

16. The CPAP apparatus of claim 13, wherein the piloted exhalation valve is closed with the pressure differential being higher relative to the pressure differential of when the piloted exhalation valve is open.

17. The CPAP apparatus of claim 13, wherein the blower controller relieves mask pressure by reducing the blower speed.

18. The CPAP apparatus of claim 13, further comprising:
a temperature sensor for a motor of the blower;
wherein a particular speed at which the motor is driven by the pressure controller to regulate the therapeutic pressure at the patient is a function of temperature readings from the temperature sensor.

19. The CPAP apparatus of claim 13, wherein the blower controller regulates therapeutic pressure delivered to the patient according to a trigger limit and a cycle limit reached by the blower speed.

20. A method for administering continuous positive airway pressure (CPAP) therapy to a patient, the method comprising:
receiving a first CPAP therapeutic pressure value;
measuring a blower speed from a blower generating a therapeutic pressure to the patient;
measuring a mask pressure value at a ventilation mask worn by the patient;
evaluating a patient respiratory state from the blower speed, the patient respiratory state being one of an inspiration state and an expiration state; and
selectively adjusting the blower speed to deliver the therapeutic pressure to the patient in response to the evaluated patient respiratory state, the speed of the blower generating a quantity of the therapeutic pressure corresponding to the first CPAP therapeutic pressure value, the selectively applied quantity of the therapeutic pressure at the ventilation mask inducing a pressure differential between the output of the blower and the ventilation mask, the ventilation mask including a piloted exhalation valve being opened and closed by selective application of fluid pressure thereto in response to the induced pressure differential.

21. The method of claim 20, further comprising:
measuring an operating speed of the blower;
measuring an operating temperature of the blower; and
modulating the blower as a function of the operating speed and the operating temperature of the blower.

22. The method of claim 20, further comprising:
generating a leak constant value from an average blower speed value over a predetermined time period.

23. The method of claim 22, further comprising:
generating a trigger limit value based upon the leak constant value summed with a trigger constant;
triggering the blower based upon the blower speed value reaching the trigger limit value;
wherein the selectively applying the quantity of the therapeutic pressure at the patient corresponds to the triggering the blower.

24. The method of claim 22, further comprising:
generating a cycle limit value based upon a cycle constant fraction of a maximum blower speed value;
cycling the blower based upon the blower speed value reaching the cycle limit value;
wherein the selectively applying the quantity of therapeutic pressure at the patient corresponds to the cycling the blower.

* * * * *